United States Patent
Kong et al.

(10) Patent No.: US 8,326,410 B2
(45) Date of Patent: Dec. 4, 2012

(54) METHOD FOR AUTOMATED ANALYSIS OF SUBMAXIMAL F-WAVES

(75) Inventors: Xuan Kong, Acton, MA (US); Pansy Bansal, Waltham, MA (US); Shai N. Gozani, Brookline, MA (US)

(73) Assignee: NeuroMetrix, Inc., Waltham, MA (US)

( * ) Notice: Subject to any disclaimer, the term of this patent is extended or adjusted under 35 U.S.C. 154(b) by 1260 days.

(21) Appl. No.: 11/265,027

(22) Filed: Nov. 2, 2005

(65) Prior Publication Data

US 2006/0217631 A1 Sep. 28, 2006

Related U.S. Application Data

(63) Continuation-in-part of application No. 10/780,118, filed on Feb. 17, 2004, now abandoned, and a continuation-in-part of application No. 11/076,789, filed on Mar. 9, 2005, now Pat. No. 7,749,171.

(60) Provisional application No. 60/624,259, filed on Nov. 2, 2004.

(51) Int. Cl.
*A61B 5/05* (2006.01)

(52) U.S. Cl. .................. 600/547; 600/557; 600/595

(58) Field of Classification Search .................. 600/547, 600/554, 557, 595
See application file for complete search history.

(56) References Cited

U.S. PATENT DOCUMENTS

| | | | |
|---|---|---|---|
| 3,572,322 A | 3/1971 | Wade | |
| 3,886,931 A | 6/1975 | Rodler | |
| 4,213,467 A | 7/1980 | Stulen et al. | |
| 4,595,018 A | 6/1986 | Rantala | |
| 4,763,666 A | 8/1988 | Strian et al. | |
| 4,807,643 A | 2/1989 | Rosier | |
| 4,811,742 A | 3/1989 | Hassel et al. | |
| 5,050,612 A | 9/1991 | Matsumura | |
| 5,080,099 A | 1/1992 | Way et al. | |
| 5,092,344 A | 3/1992 | Lee | |
| 5,099,844 A | 3/1992 | Faupel | |
| 5,131,401 A | 7/1992 | Westenskow et al. | |
| 5,143,081 A | 9/1992 | Young et al. | |
| 5,203,330 A | 4/1993 | Schaefer et al. | |
| 5,215,100 A | 6/1993 | Spitz et al. | |
| 5,255,677 A | 10/1993 | Schaefer et al. | |
| 5,327,902 A | 7/1994 | Lemmen | |
| 5,333,618 A | 8/1994 | Lekhtman et al. | |
| 5,379,764 A | 1/1995 | Barnes et al. | |
| 5,466,256 A | 11/1995 | McAdams et al. | |
| 5,467,768 A | 11/1995 | Suda et al. | |
| 5,491,627 A | 2/1996 | Zhang et al. | |

(Continued)

FOREIGN PATENT DOCUMENTS

EP 0 025 222 3/1981
(Continued)

OTHER PUBLICATIONS

"Occurrence of A-Waves in F-Wave Studies of Healthy Nerves" by Puska et al., Muscle & Nerve, vol. 28 Issue 5, pp. 626-629, Nov. 2003.*

(Continued)

*Primary Examiner* — Rene Towa
(74) *Attorney, Agent, or Firm* — Pandiscio & Pandiscio (57) ABSTRACT

A novel submaximal F-wave acquisition and analysis system that employs computational intelligence to set up submaximal F-wave acquisition conditions and to extract submaximal F-wave features automatically, without operator intervention.

40 Claims, 5 Drawing Sheets

U.S. PATENT DOCUMENTS

| | | | |
|---|---|---|---|
| 5,496,363 | A | 3/1996 | Burgio et al. |
| 5,511,553 | A | 4/1996 | Segalowitz |
| 5,540,235 | A | 7/1996 | Wilson |
| 5,560,372 | A | 10/1996 | Cory |
| 5,851,191 | A | 12/1998 | Gozani |
| 5,976,094 | A | 11/1999 | Gozani |
| 6,132,386 | A | 10/2000 | Gozani et al. |
| 6,266,558 | B1 * | 7/2001 | Gozani et al. ............ 600/547 |
| 6,379,313 | B1 | 4/2002 | Gozani et al. |
| 6,546,378 | B1 | 4/2003 | Cook |
| 6,692,444 | B2 | 2/2004 | Gozani et al. |
| 7,452,335 | B2 | 11/2008 | Wells et al. |
| 2003/0093006 | A1 * | 5/2003 | Wells et al. ............ 600/547 |
| 2006/0020222 | A1 | 1/2006 | Gozani et al. |
| 2006/0100540 | A1 | 5/2006 | Gozani et al. |

FOREIGN PATENT DOCUMENTS

| | | |
|---|---|---|
| EP | 0 436 121 | 7/1991 |
| JP | 1-259841 | 10/1989 |
| JP | 3-146028 | 6/1991 |
| JP | 7-308300 | 11/1995 |
| WO | WO 91/16001 | 10/1991 |
| WO | WO 92/03974 | 3/1992 |

OTHER PUBLICATIONS

Bischoff et al., "Significance of A-waves recorded in routine motor nerve conduction studies," Clin Neurophys 1996; 101:528-533.*

Testerman, "Method of Measuring Blood Glucose Level by Sensing Evoked Action Potentials in Peripheral Nerve", Research Disclosure, 227:92, Article No. 22728. Mar. 1983.

Oh, "Clinical Electromyography: Nerve Conduction Studies", Williams & Wilkins, 2nd Ed., 1993.

Gilliatt et al., "The Refractory and Supernormal Periods of the Human Median Nerve", J. Neurol. Neurosurg. Psychiat., 1963, 26, pp. 136-147.

Lindstrom et al., "Mechanism of Anoxic Conduction Block in Mammalian Nerve", Acta Physiol Scand, 1991, 141, pp. 429-433.

Basmajian et al., "Muscles Alive: Their Functions Revealed by Electromyography", William & Wilkins, 5th Ed., 1985.

Fujisawa et al., "Surface Electromyographic Electrode Pair With Built-In-Buffer-Amplifiers", The Journal of Prosthetic Dentistry, Mar. 1990, vol. 63, No. 3, pp. 350-352.

Seneviratne et al., "The Effect of Ischaemia on the Excitability of Human Sensory Nerve", J. Neurol. Neurosurg. Psychiat.,1968, 31, pp. 338-347.

Shefner, "The Use of Sensory Action Potentials in the Diagnosis of Peripheral Nerve Disease", Arch Neurol, Mar. 1990, vol. 47, pp. 341-348.

Stewart et al., "Substrate Changes in Peripheral Nerve During Ischaemia and Wallerian Degeneration", Journal of Neurochemistry, 1965, vol. 12, pp. 719-727.

Bischoff et al., "Significance of A-Waves Recorded in Routine Motor Nerve Conduction Studies", Electroencephalography and Clinical Neurophysiology, 1996; 101, pp. 528-533.

Bostock et al., "Changes in Excitability and Accommodation of Human Motor Axons Following Brief Periods of Ischaemia", Journal of Physiology, 1991, 441, pp. 513-535, Great Britain.

Nishimura et al., "Clinical Application of an Active Electrode Using an Operational Amplifier," IEEE Transactions on Biomedical Engineering, Oct. 1992, vol. 39, No. 10, pp. 1096-1099.

Brodie, Chata and Sampson, S.R., Contribution of Electrogenic Sodium-Potassium ATPase to Resting Membrane Potential of Cultured Rat Skeletal Myotubes, Brain Research, 1985, 28-35, 347.

Now Diagnose and Monitor the Clinical Progress of Compression Neuropathies Such as Carpal Tunnel Syndrome—in the Office or Clinic, Neuroton Medical, 1991, Lawrenceville, NJ, (product literature).

* cited by examiner

METHOD FOR AUTOMATED ANALYSIS OF SUBMAXIMAL F-WAVES

REFERENCE TO PENDING PRIOR PATENT APPLICATIONS

This patent application:

(i) is a continuation-in-part (CIP) of prior U.S. patent application Ser. No. 10/780,118, filed Feb. 17, 2004 now abandoned by Shai N. Gozani et al. for METHODS FOR THE ASSESSMENT OF NEUROMUSCULAR FUNCTION BY F-WAVE LATENCY;

(ii) is a continuation-in-part (CIP) of prior U.S. patent application Ser. No. 11/076,789, filed Mar. 9, 2005 now U.S. Pat. No. 7,749,171 by Shai N. Gozani et al. for METHOD FOR AUTOMATED DETECTION OF A-WAVES; and (iii) claims benefit of pending prior U.S. Provisional Patent Application Ser. No 60/624,259, filed Nov. 2, 2004 by Xuan Kong et al. for PERONEAL F-WAVE LATENCY UNDER SUBMAXIMAL STIMULATION.

The above-identified patent applications are hereby incorporated herein by reference.

BACKGROUND OF THE INVENTION

A nerve conduction study (NCS) is a diagnostic procedure whereby peripheral nerves are stimulated electrically and then bioelectrical potentials are recorded from the same nerve at a second location or from a muscle innervated by the activated nerve. These recorded bioelectrical potentials may, in many circumstances, provide a reliable indication of a particular medical condition.

Such nerve conduction studies often comprise both early potentials and late potentials. Early potentials reflect direct conduction from the site of stimulation to the site of recording. Late potentials represent conduction from the site of stimulation antidromically towards the spinal cord, reflection along the nerve path or within the spinal cord itself, and then conduction back down to the recording site.

The most common type of late potential recorded from a muscle innervated by the stimulated nerve is the F-wave. F-waves are highly variable waveforms that are caused by motor neuron back-firing and are generally recorded in all nerve conduction studies regardless of whether a pathology exists or not. F-wave study parameters generally include mean F-wave latency, minimum F-wave latency, maximum F-wave latency, chronodispersion, persistence, duration, F-wave amplitude, etc.

Due to the inherent variability in F-wave responses, these parameters must be established on the basis of multiple F-wave traces acquired after repetitive stimulation. Mean F-wave latency, the most robust F-wave parameter, generally requires the accumulation of at least ten individual F-wave latencies, or up to twenty stimuli, depending upon the persistence. Other parameters, such as minimum F-wave latency, may require the accumulation of even more individual F-wave latencies, as their physical attributes are typically less robust. Prior studies suggest that up to 30 F-wave latencies, or 100 stimuli, may be needed to reliably establish a number of the F-wave parameters. However, repetitive supramaximal stimulation can cause significant discomfort for some patients, thus limiting their willingness to accept high stimulus counts and, consequently, their acceptance for the procedure. More particularly, the reaction of a single muscle fiber to an electrical stimulus generally follows an all-or-nothing rule: each fiber of a muscle will either contract maximally or not at all. This means that a sufficient stimulus impulse (i.e., a "maximal stimulus") is required to ensure that substantially all of the fibers of the stimulated muscle contract. However, some patients experience significant discomfort with such supramaximal stimulation, and are therefore reluctant to undergo repetitive supramaximal stimulation. This has the effect of limiting the utility of a repetitive supramaximal stimulation procedure.

Due to the aforementioned problems associated with a repetitive supramaximal stimulation procedure, efforts have been made to conduct nerve conduction testing using late potentials evoked with submaximal stimulation.

Currently, submaximal stimulation is manually determined and performed for F-wave analysis. Typically, a clinician gradually reduces the stimulation intensity level from its supramaximal level to a submaximal level by visually monitoring the direct muscle response changes occurring in response to the reduction in stimulation intensity. Subsequent F-wave analysis under submaximal stimulation is also manually performed by the clinician to determine the F-wave latency parameters, persistence level, and amplitude.

The current approach of manual submaximal stimulation and F-wave analysis has several significant deficiencies associated therewith. More particularly, one of the deficiencies of this approach is that the subjective determination of the submaximal stimulation level is time-consuming, and thus may not be performed because of time and resource limitations. In addition, the subjective determination of the submaximal stimulation level is operator dependent and, furthermore, inter-operator variations generally do not support the standardization of the submaximal F-wave analysis: these two factors may lead to wide differences in clinical results. Furthermore, the subjective extraction of submaximal F-wave features is generally time-consuming and may not be performed because of time and resource limitations. Also, the manual subjective processing of submaximal F-wave features limits, in a practical sense, the total number of waveforms which may be studied in a particular patient study and the precision of the features determined, thus making the diagnostic value of the F-wave studies less reliable.

SUMMARY OF THE INVENTION

To overcome the foregoing deficiencies and limitations associated with prior art submaximal F-wave studies, a novel automated submaximal stimulation F-wave acquisition and analysis system has now been developed. Among other things, this novel system:

(i) eliminates the need for the tedious, inefficient and error-prone process of manually determining submaximal F-wave stimulation;

(ii) facilitates the collection of a large number of F-waves under repetitive stimulation so that a reliable estimation of the F-wave features can be obtained;

(iii) ensures consistent F-wave feature determination, thus providing standardization of the F-wave analysis across electrodiagnostic studies, including those performed in multiple sites by different clinicians;

(iv) supports the automated extraction of F-wave features from a large number of F-wave waveforms so as to enhance the clinical utilities of the existing F-wave features; and (v) enables the reliable estimation of F-wave features not readily observable in a given time domain so as to expand the clinical utility of the F-wave analysis.

In one form of the present invention, there is provided a method for acquiring and analyzing F-waves under a submaximal stimulation condition, the method comprising:

(i) applying a series of stimuli of variable intensity to a nerve;
(ii) recording a series of early responses;
(iii) determining a submaximal stimulation level for F-wave acquisition and analysis;
(iv) applying a series of stimuli of submaximal intensity to a nerve;
(v) recording a series of late responses;
(vi) regulating the submaximal stimulation and acquisition condition based on late response features;
(vii) analyzing late response to regulate the processing condition of F-wave features; and
(viii) characterizing F-wave features with trace-by-trace and/or total waveform set analysis.

In another form of the present invention, there is provided a method for diagnosing a disorder in a patient comprising:
(i) applying a series of stimuli of variable intensity to a nerve;
(ii) recording a series of early responses;
(iii) determining a submaximal stimulation level for F-wave acquisition and analysis;
(iv) applying a series of stimuli of submaximal intensity to a nerve;
(v) recording a series of late responses;
(vi) regulating the submaximal stimulation and acquisition condition based on late response features;
(vii) analyzing late responses to regulate the processing condition of F-wave features;
(viii) characterizing F-wave features with trace-by-trace and/or total waveform set analysis; and
(ix) comparing F-wave characteristics based on the submaximal late responses with those of normal character and those of known disorder.

In another form of the present invention, there is provided a system for analyzing submaximal F-waves comprising:
(i) a stimulation electrode;
(ii) a stimulation circuit connected to the stimulation electrode for applying a series of stimuli to a nerve;
(iii) a detection electrode;
(iv) a detection circuit connected to the detection electrode; and
(v) an analyzer connected to the detection circuit and stimulation circuit and adapted to conduct submaximal F-wave analysis by:
  (a) recording a series of early responses detected by the detection circuit and evoked by stimuli with variable intensities delivered by the stimulation circuit;
  (b) determination of a submaximal stimulation level based on an early response feature space;
  (c) recording a series of late responses detected by the detection circuit and evoked by submaximal stimulation;
  (d) regulating the stimulation circuit by the analyzer based on late response features;
  (e) recording and analyzing a series of late responses detected by the detection circuit; and
  (f) altering the F-wave analysis setup and late response traces; and
(vi) apparatus for characterizing the F-wave features.

In another form of the present invention, there is provided a method for submaximal F-wave acquisition and analysis, the method comprising:
(i) applying a series of stimuli of increasing intensity to a nerve;
(ii) recording a series of early responses;
(iii) determining the submaximal stimulation intensity based on a stimulus response curve and a target ratio between the submaximal and supramaximal early response magnitudes;
(iv) applying a series of stimuli of fixed intensity at the submaximal level to the nerve;
(v) recording a series of late responses;
(vi) detecting possible A-wave and H-reflex responses and excluding those segments from the late responses; and
(vii) extracting F-wave parameters from the remaining late wave segments.

In another form of the present invention, there is provided a method for submaximal F-wave acquisition and analysis, the method comprising:
(i) applying a series of stimuli of increasing intensity to a nerve;
(ii) recording a series of early responses;
(iii) determining the submaximal stimulation intensity based on a percentage or magnitude reduction of the supramaximal stimulation intensity;
(iv) applying a series of stimuli of fixed intensity at the submaximal level to the nerve;
(v) recording a series of late responses;
(vi) detecting possible A-wave and H-reflex responses and excluding those waveform segments from the late responses; and
(vii) extracting F-wave parameters from the remaining late wave segments.

In another form of the present invention, there is provided a method for submaximal F-wave acquisition and analysis, the method comprising:
(i) applying a series of stimuli of increasing intensity to a nerve;
(ii) recording a series of early responses;
(iii) determining the submaximal stimulation intensity based on a percentage or magnitude reduction of the supramaximal early response magnitude;
(iv) applying a series of stimuli of fixed intensity at the submaximal level to the nerve;
(v) recording a series of late responses;
(vi) detecting possible A-wave and H-reflex responses and excluding those waveform segments from the late responses;
(vii) applying a series of stimuli with an increased level of intensity capable of suppressing axon-reflex and/or H-reflex in the late responses;
(viii) recording a series of late responses; and
(ix) determining the F-wave characteristics based on the late responses.

In another form of the present invention, there is provided a method for submaximal F-wave acquisition and analysis, the method comprising:
(i) applying a series of stimuli of increasing intensity to a nerve;
(ii) recording a series of early responses;
(iii) determining the submaximal stimulation intensity based on a stimulus response curve and a target ratio between the submaximal and supramaximal early response magnitudes;
(iv) applying a series of stimuli of fixed intensity at the submaximal level to the nerve;
(v) recording a series of late responses;
(vi) detecting possible A-wave and H-reflex responses and excluding those waveform segments from the late responses;
(vii) extracting F-wave features from the late responses;
(viii) applying a series of stimuli of fixed intensity at a higher level to the nerve;
(ix) recording a series of late responses;

(x) detecting possible A-wave and H-reflex responses and excluding those waveform segments from the late responses;

(xi) extracting F-wave features from the late responses; and (xii) conducting a comparison analysis of F-wave features from lower and higher stimulation intensities.

In another form of the present invention, there is provided a method for acquiring submaximal F-wave features, comprising:

(i) determining the stimulation intensity levels for submaximal F-wave acquisition;

(ii) acquiring and analyzing late waves under submaximal stimulation conditions;

(iii) modifying the stimulation conditions based on real-time monitoring of the late wave analysis outcomes; and (iv) extracting and comparing F-wave features under alternative stimulation conditions.

In another form of the present invention, there is provided an apparatus for acquiring submaximal F-wave features, comprising:

(i) a unit for determining the stimulation intensity levels for submaximal F-wave acquisition;

(ii) a unit for acquiring and analyzing late waves under submaximal stimulation conditions;

(iii) a unit for modifying the stimulation conditions based on real-time monitoring of the late wave analysis outcomes; and (iv) a unit for extracting and comparing F-wave features under alternative stimulation conditions.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts and further wherein.

DETAILED DESCRIPTION OF THE PREFERRED EMBODIMENTS

Electrical stimulation of many peripheral nerves (e.g., median, ulnar, peroneal, tibial, etc.) evokes both an "early response" and a "late response". The early response is characterized by orthodromic conduction of the impulse, neuromuscular junction properties, the recording electrode size, the recording electrode location, etc. The late response is characterized by antidromic (i.e., retrograde) conduction of the evoked impulse from the point of stimulation to the spinal cord, reflection of the impulse in a subset of the motor neurons, and orthodromic conduction of the impulse to a location on that nerve or to the muscle or muscles innervated by the nerve, among other things.

The late response may have several components associated therewith. The F-wave is the component of the late response which is most commonly associated with a muscle recording. The F-wave represents motor neuron backfiring. Its characteristics are affected by the conduction properties of the peripheral nerve fibers, the condition of the nerve roots at the spine, and the excitability of motor neuron pool and central nervous system, among other things. The utility of F-waves has been demonstrated in multiple clinical applications, and the stimulation of the nerve for F-wave analysis is typically performed at supramaximal intensity.

In contrast, the present invention utilizes submaximal stimulation intensities for F-wave analysis.

More particularly, the novel submaximal F-wave acquisition and analysis system of the present invention uses submaximal intensities, and employs computational intelligence to set up submaximal F-wave acquisition conditions and to extract submaximal F-wave features automatically, without operator intervention.

Figure 1:
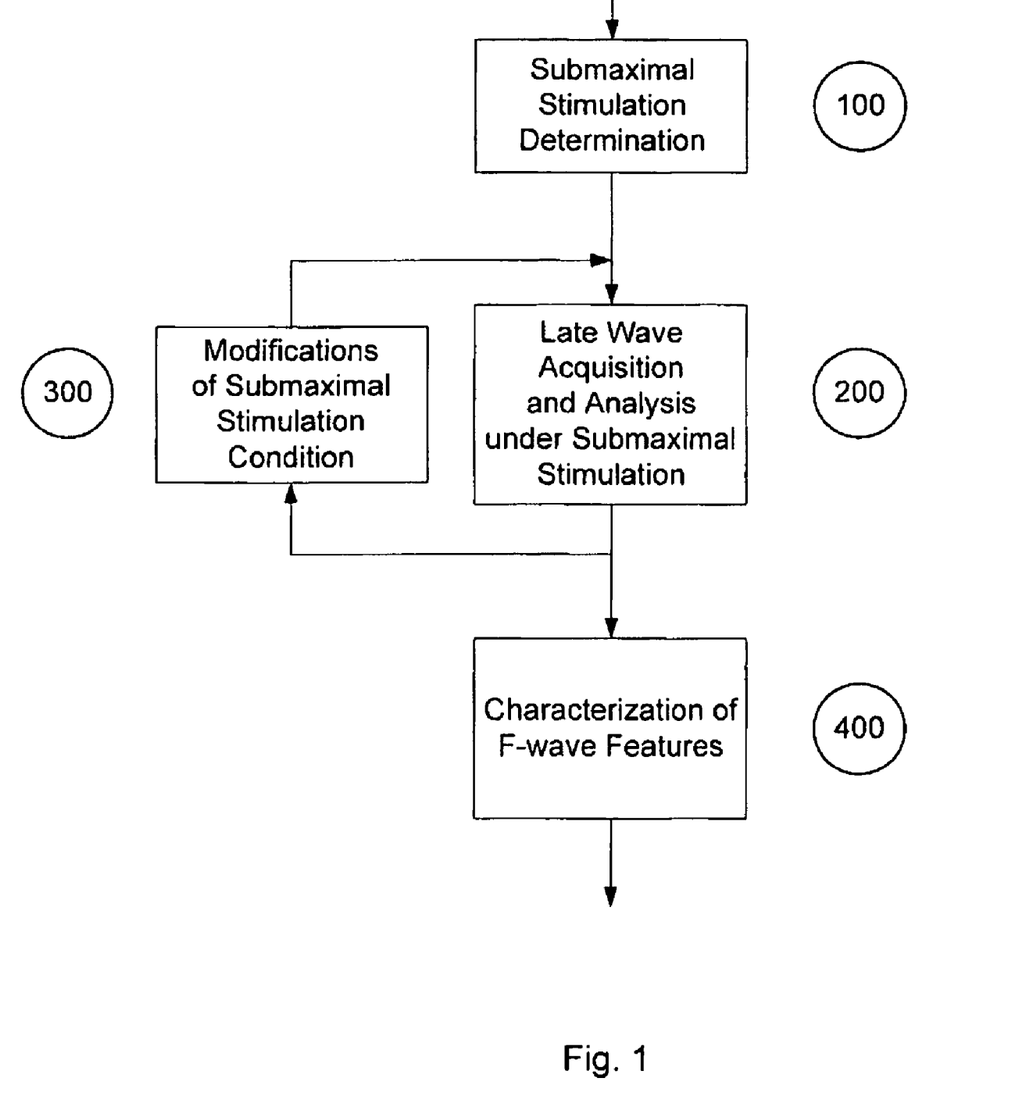
FIG. 1 is a schematic chart showing the acquisition of late waves and the analysis of F-wave features based on the late waves.

In one preferred embodiment of the present invention, and looking now at FIG. 1, the system comprises four steps:

(i) Submaximal Stimulation Determination 100—the determination of the stimulation intensity levels for submaximal F-wave acquisition;

(ii) Late Wave Acquisition And Analysis Under Submaximal Stimulation 200—the acquisition and analysis of late waves under submaximal stimulation conditions;

(iii) Modifications Of Submaximal Stimulation Condition 300—the modification of the stimulation conditions based on real-time monitoring of the late wave analysis outcomes; and (iv) Characterization Of F-wave Features 400—the extraction and comparison of F-wave features under alternative stimulation conditions.

(i) Submaximal Stimulation Determination 100

In the first step, the stimulation intensity levels are determined for submaximal F-wave acquisition. This is done by acquiring a series of early responses and analyzing their waveform features so as to determine a submaximal stimulation intensity level.

Figure 2:
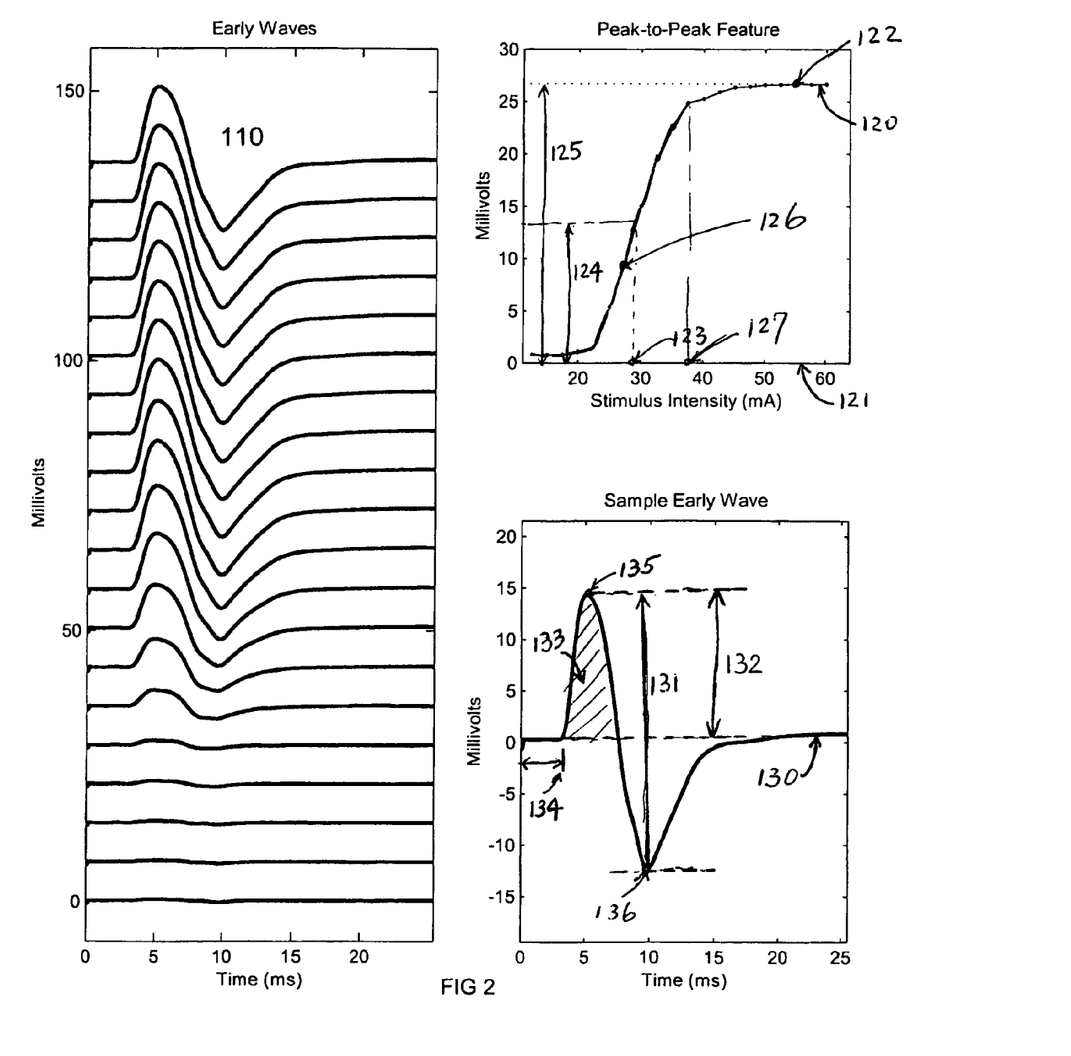
FIG. 2 are schematic graphs showing one preferred translation function for translating early responses into a submaximal stimulation condition.
Figure 3:
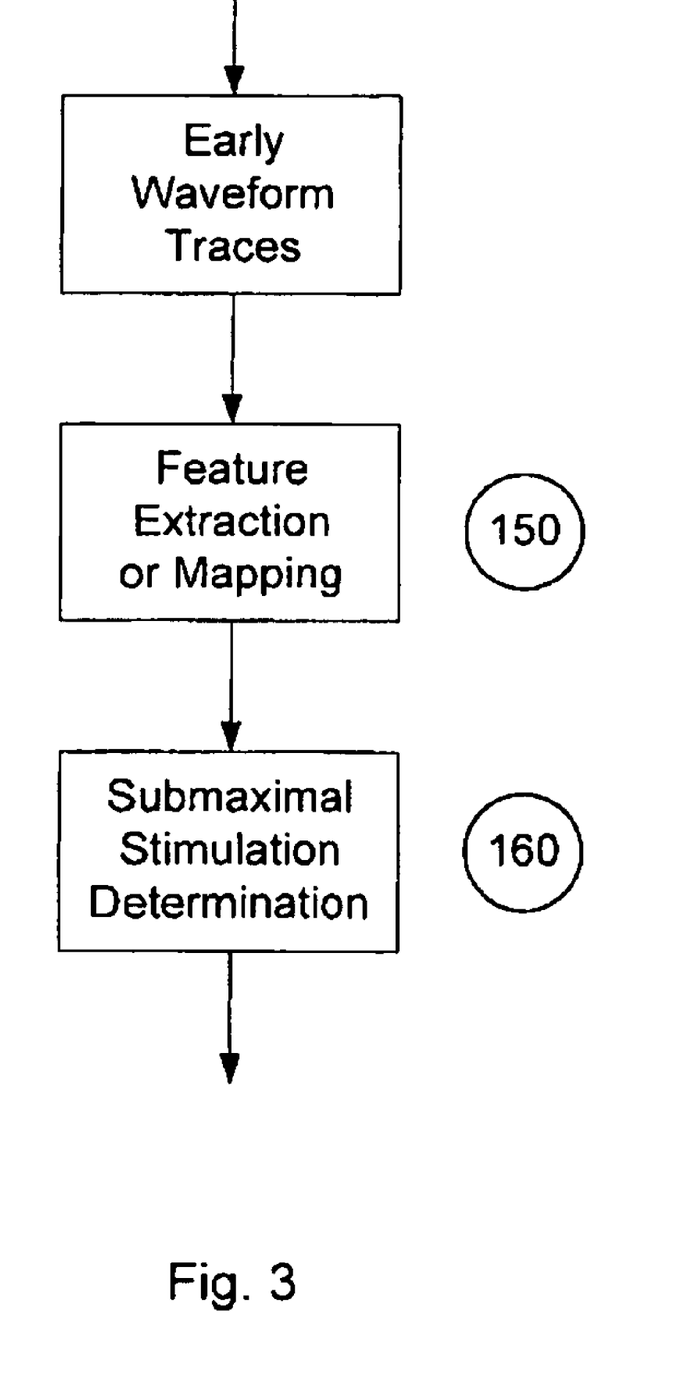
FIG. 3 is a schematic chart showing how the early waves may be translated into features for submaximal stimulation condition determination.

More particularly, the translation of an early response waveform into a feature space is shown in FIG. 2. The early response traces 110 are created by applying a series of electrical stimuli of varying intensity to a patient's peripheral nerve, with the patient responses being recorded as a series of traces by detection electrodes. Early response traces 110 are then translated by a feature extraction or mapping function 150 (FIG. 3) into a feature space 120 (FIG. 2) based on an individual trace or multiple traces. The feature space 120 forms the basis for submaximal stimulation determination 160 (FIG. 3). The translation function yields a feature 131 (FIG. 2) which represents the overall trace dynamic range (i.e., peak-to-peak amplitude) that represents the difference between the amplitudes at discrete points 135 and 136.

A map of the feature space 120 (FIG. 2) may be created from one or more of the various features (e.g., 131, 132, 133, 134, 135, 136, etc.) associated with the early response traces. More particularly, in one preferred embodiment of the present invention, and as shown in FIG. 2, the feature space map may be created using global maximum 135 and minimum 136 within each early response trace. In alternative embodiments of the present invention, other early response trace characteristics and attributes may be used to construct the feature space. By way of example but not limitation, such characteristics may include the magnitude of local maxima 132 and local minima of various linear and non-linear translations of the response trace 130, including its first derivative, its second derivative, its absolute value, and its second power. Although in the preferred embodiment of the present invention the attribute of the maxima or minima that is mapped into the feature space is its amplitude, other attributes could also be utilized. By way of example but not limitation, such attributes may include area 133, absolute value, and/or the second power of the amplitude.

In the embodiment described above, the feature space consists of two dimensions: the stimulus intensity 121 at which the early response trace was acquired; and the corresponding traces' peak-to-peak amplitude 131. Higher dimensional feature spaces may also be used in alternative embodiments of the present invention. For example, a third dimension representing the onset time of the early response activity 134 (i.e., the time difference between the initial deflection from baseline and the stimulus time, also known in the art of electrophysiology as "distal motor latency" or "DML") may also be incorporated.

Once the feature space is constructed, the submaximal stimulation level may be determined by the function 160 (FIG. 3). Function 160 translates samples in the feature space into a submaximal stimulation level so as to yield target stimulus intensity 123. More particularly, in one preferred embodiment of the present invention, the feature space map may be created using global maximum feature 122 and a specified target ratio of 50% in order to determine a desired intensity with projected feature value 124 that is 50% of the known value 125 of feature 122. Significantly, the translation result 123 does not have to be one of the stimulus intensities used to create the feature space. In additional embodiments of the present invention, other feature space attributes may be used to determine the target submaximal stimulation intensity. By way of example but not limitation, such attributes may include the intensity 126 that yields the maximum change in feature value and the intensity 127 that yields a negligible change from the maximum.

Thus, in the aforementioned first step 100, a series of electrical stimuli of varying intensities are applied to the patient, so as to evoke a series of early responses; these early responses are then analyzed (e.g., by extracting feature attributes and mapping them to a feature space, and then operating on the feature space map) so as to determine a submaximal stimulation level.

(ii) Late Wave Acquisition and Analysis Under Submaximal Stimulation 200

In the second step, a series of late responses are acquired with submaximal stimulation and the features of the late responses are translated on a trace-by-trace basis, e.g., such as is disclosed in pending prior U.S. patent application Ser. No. 10/780,118, filed Feb. 17, 2004 by Shai N. Gozani et al. for METHODS FOR THE ASSESSMENT OF NEUROMUSCULAR FUNCTION BY F-WAVE LATENCY (Attorney Docket No. NEURO-NRO-001CP1CN3), which patent application is hereby incorporated herein by reference.

Figure 4:
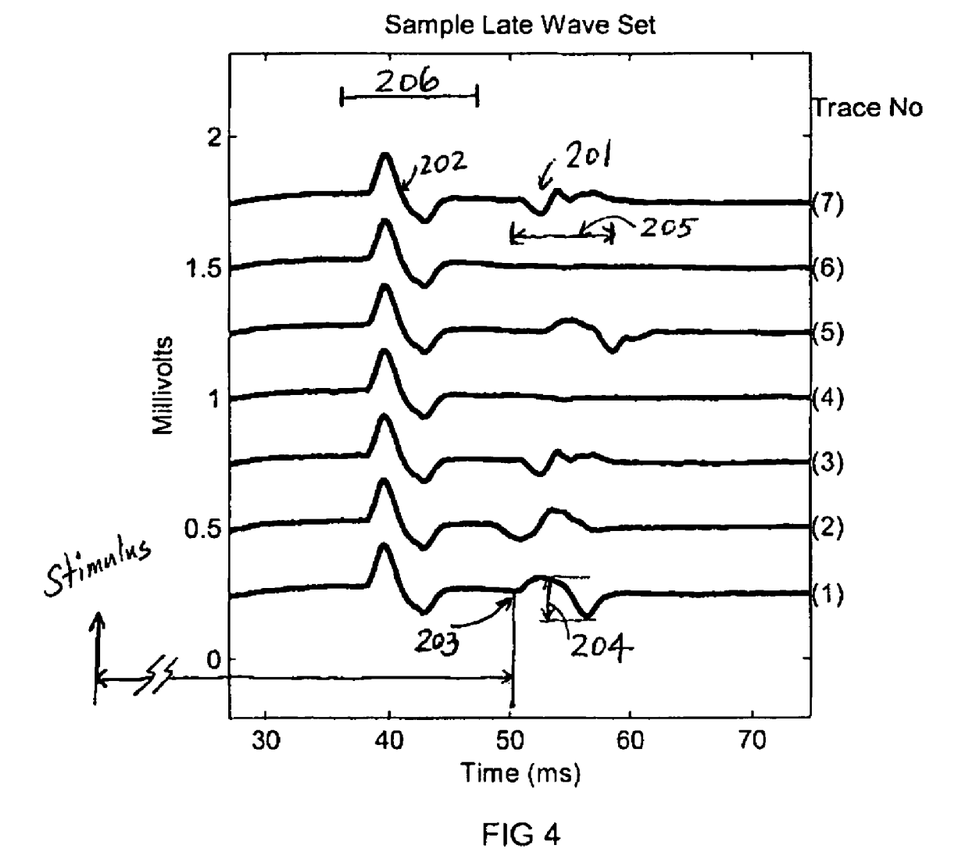
FIG. 4 is schematic graph illustrating a sample late wave set.

By way of example but not limitation, as illustrated in FIG. 4, the trace-by-trace translation of the features of the late responses may yield features like the presence/absence of F-wave 201, the presence/absence of A-wave 202, the F-wave latency 203 (if the F-wave is present), the F-wave amplitude 204, the F-wave duration 205, and other features.

Alternatively, and/or additionally, the features of the late responses may also be translated on a whole set basis. See, for example, U.S. patent application Ser. No. 11/076,789, filed Mar. 9, 2005 by Shai N. Gozani et al. for METHOD FOR AUTOMATED DETECTION OF A-WAVES (Attorney Docket No. NEURO-5), which patent application is hereby incorporated herein by reference.

By way of example but not limitation, the features of the late responses translated on the basis of whole trace sets may include, among others, persistence (percentage of traces with one or more F-waves), mean F-wave latency (mean value of all F-wave latencies in the trace set), and/or other features.

(iii) Modifications of Submaximal Stimulation Condition 300

In the third step, the late wave features are monitored in real-time via function 300 (see FIG. 1). Function 300 translates the late wave features into a supervisory control signal for possible modifications of the late wave acquisition and analysis process. In other words, function 300 may be used to analyze the late wave features and, on the basis of this analysis, modify the submaximal stimulation so as to enhance late wave features and thereby increase the utility of the late wave traces.

Figure 5:
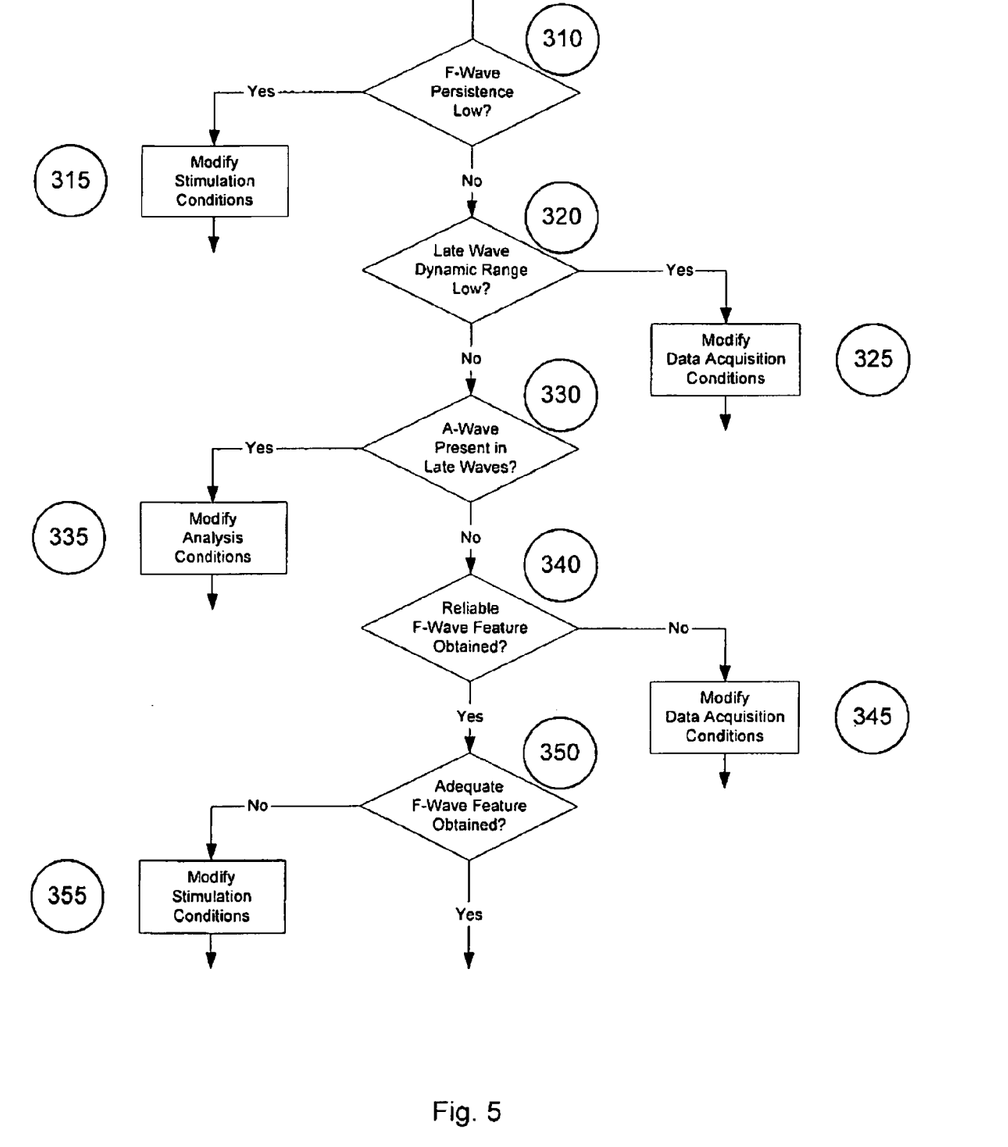
FIG. 5 is a schematic chart showing how late wave features may be monitored in real time.

A more detailed illustration of function 300 is shown in FIG. 5.

As seen in FIG. 5, the function 300 preferably consists of a series of logic tests (e.g., tests 310, 320, 330, 340 and 350) and a plurality of functions (e.g., 315, 325, 335, 345 and 355).

Function 315 regulates the stimulation condition so as to increase the persistence, i.e., if the submaximal F-wave persistence is determined to be low. In the preferred embodiment of the present invention, the stimulation condition is changed with increased stimulus intensity. In alternative embodiments of the present invention, other changes in stimulation conditions may be included, e.g., an increase in stimulus frequency, a combination of an increase in both stimulus intensity and frequency, etc.

Function 325 regulates the data acquisition condition to improve the dynamic range of recorded late wave traces. In one preferred embodiment of the present invention, the signal amplification gain is increased so as to enhance the dynamic range. Other changes in the late wave acquisition condition may be an increase in waveform representation resolution, a modification of the waveform filtering setting, and/or a combination of both of these changes.

Function 335 regulates the late wave analysis conditions by modifying the waveform region of analysis for F-wave feature analysis functions. In one preferred embodiment of the present invention, waveform segment 206 (FIG. 4) containing A-waves is excluded from consideration in the F-wave feature analysis. In addition, other modifications may be considered, for example, removing A-wave components from the late wave traces, etc.

Function 345 regulates the acquisition conditions by modifying the number of late waves and the region of the late wave recordings. In one preferred embodiment of present invention, the waveform acquisition may be terminated earlier if a sufficient number of F-waves with high-quality features is obtained. Other possible modifications may include extending the waveform acquisition window so as to include prolonged components of F-waves, expanding the acquisition wave count for late wave sets with high variability in F-wave features, etc.

Function 355 regulates the acquisition and stimulation conditions based on F-wave feature characteristics. In one preferred embodiment of the present invention, stimulus intensity may be increased if F-wave latency features (e.g., mean F-wave latencies) are prolonged. The pre-determined stimulation count is preferably reduced if the F-wave features are conclusive, with high quality, when the F-wave features are compared with reference range values. Other possible modifications may include extending the waveform acquisition window to include delayed components of the F-waves, expanding the acquisition wave count for late wave sets with high variability in F-wave features, etc.

(iv) Characterization of F-wave Features 400

In step four, the set of F-waves acquired and analyzed is characterized by a set of features, whereby to achieve a neuropathy diagnosis. One standard feature is the mean F-wave latency. The mean F-wave latency obtained under submaximal stimulation condition is known in the art of electrodiagnostics to be equivalent to that obtained under supramaximal condition. By way of example but not limitation, other F-wave features may include minimum latency, maximum latency, chronodispersion, persistence, duration, amplitude, etc. Further examples of features include the complexity of the F-wave as measured by the number of phases in the F-wave components and the coherence of the F-wave as measured by the similarity (in time, in morphology, and in size) among the F-wave components in different late wave traces. The occurrence rate of the F-wave features in a late wave ensemble (e.g., persistence), as well as the characteristics of these F-waves, may be used as is known in the art to diagnose neurophathic conditions. For example, prolonged F-wave latencies are a sensitive abnormality in polyneuropathies, persistence is indicative of the excitability changes in the motor neuron pool and central nervous system, etc.

Modifications

It will be appreciated that still further embodiments of the present invention will be apparent to those skilled in the art in view of the present disclosure. It is to be understood that the present invention is by no means limited to the particular constructions herein disclosed and/or shown in the drawings, but also comprises any modifications or equivalents within the scope of the invention.

What is claimed is:

1. A method for acquiring and analyzing F-waves under a submaximal stimulation condition, the method comprising:
    (i) applying a series of stimuli of variable intensity to a nerve using a stimulation electrode;
    (ii) recording a series of early responses;
    (iii) determining a submaximal stimulation level for F-wave acquisition and analysis, wherein the submaximal stimulation level is an intensity level which is approximately fifty percent of a maximal stimulus intensity, and further wherein the maximal stimulus intensity is an intensity level at which additional increases in stimulus intensity do not lead to further increases in the amplitude of an evoked response;
    (iv) applying a series of stimuli to a nerve using the stimulation electrode, wherein the series of stimuli are applied at the submaximal stimulation level;
    (v) recording a series of late responses;
    (vi) regulating the submaximal stimulation level and acquisition condition based on late response features;
    (vii) analyzing late response to regulate a processing condition of F-wave features; and
    (viii) characterizing F-wave features with trace-by-trace and/or total waveform set analysis.

2. A method according to claim 1 wherein the determination of the submaximal stimulation level is based on an early wave feature space.

3. A method according to claim 2 wherein the feature space is based on a translation of an early wave into a feature space.

4. A method according to claim 3, wherein the translation comprises the step of determining the local minima, local maxima, first deflection from baseline, and subsequent crossings of baseline level for the individual early responses.

5. A method according to claim 3, wherein the translation comprises the step of determining the local minima, local maxima, and zero crossings of the first and second order derivatives of the early responses.

6. A method according to claim 3, wherein the translation comprises the step of determining linear translation of the early responses.

7. A method according to claim 3, wherein the translation comprises the step of determining nonlinear translation of the early responses.

8. A method according to claim 2 wherein the determination of the submaximal stimulation level is based on one or more features as the result of one or more translation.

9. A method according to claim 8 wherein the determination further comprises the step of determining reference feature values in the feature space.

10. A method according to claim 8 wherein the determination further comprises the step of determining target feature values associated with a target submaximal stimulation level.

11. A method according to claim 8 wherein the determination further comprises the step of determining a target stimulation intensity based on feature space characteristics.

12. A method according to claim 8 wherein the determination further comprises the step of determining of target stimulation intensity based on at least one selected from the group consisting of prediction, smoothing, interpolation, and estimation.

13. A method according to claim 1 wherein the late response feature comprises at least one selected from the group consisting of: F-wave persistence, F-wave amplitude and its relationship with available dynamic range, F-wave morphology, A-wave presence, artifacts commonly observed in late waves, and baseline fluctuation.

14. A method according to claim 1 wherein the step of regulating comprises the actions of changing at least one stimulation and acquisition condition selected from the group consisting of: stimulation intensity, stimulation frequency, stimulation duration, late wave acquisition gain, digital waveform amplitude representation resolution, analog-to-digital bits per sample, digital waveform time scale representation resolution, sampling interval, analog and digital filter settings for conditioning late wave before display and feature analysis, and data acquisition window starting time and duration.

15. A method according to claim 1 wherein the step of regulating comprises the detection and localization of A-wave components.

16. A method according to claim 1 wherein the step of regulating comprises:
    (a) masking A-wave segments of late responses from F-wave feature analysis;
    (b) removing A-wave components from late responses prior to F-wave feature analysis; and
    (c) altering F-wave feature analysis method settings to minimize the interference of A-wave components.

17. A method according to claim 1 wherein applying a series of stimuli of variable intensity to a nerve comprises applying a series of stimuli of increasing intensity to a nerve.

18. A method according to claim 1 wherein determining a submaximal stimulation level for F-wave acquisition and analysis comprises determining the submaximal stimulation intensity based on a stimulus response curve and a target ratio between the submaximal and supramaximal early response magnitudes.

19. A method according to claim 1 wherein applying a series of stimuli of submaximal intensity to a nerve comprises applying a series of stimuli of fixed intensity at the submaximal level to the nerve.

20. A method according to claim 1 wherein regulating the submaximal stimulation level and acquisition condition based on late response features comprises detecting possible A-wave and H-reflex responses and altering the stimulation condition to suppress or enhance such responses.

21. A method according to claim 20 wherein detecting possible A-wave and H-reflex responses and altering the stimulation condition to suppress the A-wave and H-reflex responses from the late responses comprises applying a series of stimuli with an increased level of intensity capable of suppressing axon-reflex and/or H-reflex in the late response.

22. A method according to claim 1 wherein analyzing late responses to regulate the processing condition of F-wave features comprises excluding A-wave and H-reflex response segments from the late wave and extracting F-wave parameters from the remaining late wave segments.

23. A method according to claim 1 wherein determining a submaximal stimulation level for F-wave acquisition and analysis comprises determining the submaximal stimulation intensity based on a percentage or magnitude reduction of a supramaximal stimulation intensity.

24. A method according to claim 1 wherein determining a submaximal stimulation level for F-wave acquisition and analysis comprises determining the submaximal stimulation intensity based on a percentage or magnitude reduction of a supra maximal early response magnitude.

25. A method according to claim 1 wherein applying a series of stimuli of variable intensity to a nerve comprises applying a series of stimuli of intensities that are determined based on an efficient search algorithm.

26. A method for diagnosing a disorder in a patient comprising:
 (i) applying a series of stimuli of variable intensity to a nerve using a stimulation electrode;
 (ii) recording a series of early responses;
 (iii) determining a submaximal stimulation level for F-wave acquisition and analysis, wherein the submaximal stimulation level is an intensity level which is approximately fifty percent of a maximal stimulus intensity, and further wherein the maximal stimulus intensity is an intensity level at which additional increases in stimulus intensity do not lead to further increases in the amplitude of an evoked response;
 (iv) applying a series of stimuli to a nerve using the stimulation electrode, wherein the series of stimuli are applied at the submaximal stimulation level;
 (v) recording a series of late responses;
 (vi) regulating the submaximal stimulation level and acquisition condition based on late response features;
 (vii) analyzing late responses to regulate the processing condition of F-wave features;
 (viii) characterizing F-wave features with trace-by-trace and/or total waveform set analysis; and
 (ix) comparing F-wave characteristics based on the submaximal late responses with those of normal character and those of known disorder.

27. A system for analyzing F-waves acquired under submaximal stimulation conditions, the system comprising:
 (i) a stimulation electrode;
 (ii) a stimulation circuit connected to the stimulation electrode for applying a series of stimuli to a nerve;
 (iii) a detection electrode;
 (iv) a detection circuit connected to the detection electrode; and
 (v) an analyzer connected to the detection circuit and stimulation circuit and adapted to conduct submaximal F-wave analysis by:
  (a) recording a series of early responses detected by the detection circuit and evoked by stimuli with variable intensities delivered by the stimulation circuit;
  (b) determination of a submaximal stimulation level based on an early response feature space, wherein the submaximal stimulation level is an intensity level which is approximately fifty percent of a maximal stimulus intensity, and further wherein the maximal stimulus intensity is an intensity level at which additional increases in stimulus intensity do not lead to further increases in the amplitude of an evoked response;
  (c) recording a series of late responses detected by the detection circuit and evoked by submaximal stimulation;
  (d) regulating the stimulation circuit by the analyzer based on late response features;
  (e) recording and analyzing a series of late responses detected by the detection circuit; and
  (f) altering the F-wave analysis setup and late response traces; and
 (vi) apparatus for characterizing the F-wave features.

28. A method for acquiring submaximal F-wave features, comprising:
 (i) determining a submaximal stimulation level for submaximal F-wave acquisition, wherein the submaximal stimulation level is an intensity level which is approximately fifty percent of a maximal stimulus intensity, and further wherein the maximal stimulus intensity is an intensity level at which additional increases in stimulus intensity do not lead to further increases in the amplitude of an evoked response;
 (ii) acquiring and analyzing late waves, using a stimulation electrode and a detection electrode, under submaximal stimulation conditions;
 (iii) modifying the stimulation conditions based on real-time monitoring of the late wave analysis outcomes; and
 (iv) extracting and comparing F-wave features under alternative stimulation conditions.

29. Apparatus for acquiring submaximal F-wave features, comprising:
 (i) a unit for determining a submaximal stimulation level for submaximal F-wave acquisition, wherein the submaximal stimulation level is an intensity level which is approximately fifty percent of a maximal stimulus intensity, and further wherein the maximal stimulus intensity is an intensity level at which additional increases in stimulus intensity do not lead to further increases in the amplitude of an evoked response;
 (ii) a unit for acquiring and analyzing late waves under submaximal stimulation conditions;
 (iii) a unit for modifying the stimulation conditions based on real-time monitoring of the late wave analysis outcomes; and
 (iv) a unit for extracting and comparing F-wave features under alternative stimulation conditions.

30. A method for acquiring and analyzing F-waves under a submaximal stimulation condition, the method comprising:
- (i) applying a series of stimuli of variable intensity to a nerve using a stimulation electrode;
- (ii) recording a series of early responses;
- (iii) determining a submaximal stimulation level for F-wave acquisition and analysis wherein the submaximal stimulation level is an intensity level which is approximately fifty percent of a maximal stimulus intensity, and further wherein the maximal stimulus intensity is an intensity level at which additional increases in stimulus intensity do not lead to further increases in the amplitude of an evoked response;
- (iv) applying a series of stimuli of submaximal intensity to a nerve using the stimulation electrode;
- (v) recording a series of late responses;
- (vi) regulating the submaximal stimulation and acquisition condition based on late response features;
- (vii) analyzing late response to regulate a processing condition of F-wave features; and
- (viii) characterizing F-wave features with trace-by-trace and/or total waveform set analysis;
- wherein the determination of the submaximal stimulation level is based on an early wave feature space;
- wherein the feature space is based on a translation of an early wave into a feature space; and
- wherein the translation comprises the step of determining the local minima, local maxima, first deflection from baseline, and subsequent crossings of baseline level for the individual early responses.

31. A method for acquiring and analyzing F-waves under a submaximal stimulation condition, the method comprising:
- (i) applying a series of stimuli of variable intensity to a nerve using a stimulation electrode;
- (ii) recording a series of early responses;
- (iii) determining a submaximal stimulation level for F-wave acquisition and analysis wherein the submaximal stimulation level is an intensity level which is approximately fifty percent of a maximal stimulus intensity, and further wherein the maximal stimulus intensity is an intensity; level at which additional increases in stimulus intensity do not lead to further increases in the amplitude of an evoked response
- (iv) applying a series of stimuli of submaximal intensity to a nerve using the stimulation electrode;
- (v) recording a series of late responses;
- (vi) regulating the submaximal stimulation and acquisition condition based on late response features;
- (vii) analyzing late response to regulate a processing condition of F-wave features; and
- (viii) characterizing F-wave features with trace-by-trace and/or total waveform set analysis;
- wherein the determination of the submaximal stimulation level is based on an early wave feature space;
- wherein the feature space is based on a translation of an early wave into a feature space; and
- wherein the translation comprises the step of determining the local minima, local maxima, and zero crossings of the first and second order derivatives of the early responses.

32. A method for acquiring and analyzing F-waves under a submaximal stimulation condition, the method comprising:
- (i) applying a series of stimuli of variable intensity to a nerve using a stimulation electrode;
- (ii) recording a series of early responses;
- (iii) determining a submaximal stimulation level for F-wave acquisition and analysis wherein the submaximal stimulation level is an intensity level which is approximately fifty percent of a maximal stimulus intensity, and further wherein the maximal stimulus intensity is an intensity level at which additional increases in stimulus intensity do not lead to further increases in the amplitude of an evoked response;
- (iv) applying a series of stimuli of submaximal intensity to a nerve using the stimulation electrode;
- (v) recording a series of late responses;
- (vi) regulating the submaximal stimulation and acquisition condition based on late response features;
- (vii) analyzing late response to regulate a processing condition of F-wave features; and
- (viii) characterizing F-wave features with trace-by-trace and/or total waveform set analysis;
- wherein the step of regulating comprises:
  - (a) masking A-wave segments of late responses from F-wave feature analysis;
  - (b) removing A-wave components from late responses prior to F-wave feature analysis; and
  - (c) altering F-wave feature analysis method settings to minimize the interference of A-wave components.

33. A method for acquiring and analyzing F-waves under a submaximal stimulation condition, the method comprising:
- (i) applying a series of stimuli of variable intensity to a nerve using a stimulation electrode;
- (ii) recording a series of early responses;
- (iii) determining a submaximal stimulation level for F-wave acquisition and analysis wherein the submaximal stimulation level is an intensity level which is approximately fifty percent of a maximal stimulus intensity, and further wherein the maximal stimulus intensity is an intensity level at which additional increases in stimulus intensity do not lead to further increases in the amplitude of an evoked response;
- (iv) applying a series of stimuli of submaximal intensity to a nerve using the stimulation electrode;
- (v) recording a series of late responses;
- (vi) regulating the submaximal stimulation and acquisition condition based on late response features;
- (vii) analyzing late response to regulate a processing condition of F-wave features; and
- (viii) characterizing F-wave features with trace-by-trace;
- wherein regulating the submaximal stimulation and acquisition condition based on late response features comprises detecting possible A-wave and H-reflex responses and altering the stimulation condition to suppress or enhance such responses.

34. A method according to claim 33 wherein detecting possible A-wave and H-reflex responses and altering the stimulation condition to suppress the A-wave and H-reflex responses from the late responses comprises applying a series of stimuli with an increased level of intensity capable of suppressing axon-reflex and/or H-reflex in the late response.

35. A method according to claim 33 wherein analyzing late responses to regulate the processing condition of F-wave features comprises excluding A-wave and H-reflex response segments from the late wave and extracting F-wave parameters from the remaining late wave segments.

36. A method for acquiring and analyzing F-waves under a submaximal stimulation condition, the method comprising:
- (i) applying a series of stimuli of variable intensity to a nerve using a stimulation electrode;
- (ii) recording a series of early responses;
- (iii) determining a submaximal stimulation level for F-wave acquisition and analysis, wherein the submaximal stimulation level is an intensity level which is approximately fifty percent of a maximal stimulus intensity, and further wherein the maximal stimulus intensity is an intensity level at which additional increases in stimulus intensity do not lead to further increases in the amplitude of an evoked response;
(iv) applying a series of stimuli to a nerve, using the stimulation electrode, wherein the series of stimuli are applied at the submaximal stimulation level;
(v) recording a series of late responses;
(vi) regulating the submaximal stimulation level and acquisition condition based on late response features;
(vii) analyzing late response to regulate a processing condition of F-wave features; and
(viii) characterizing F-wave features with trace-by-trace and/or total waveform set analysis.

37. A method for diagnosing a disorder in a patient comprising:
(i) applying a series of stimuli of variable intensity to a nerve using a stimulation electrode;
(ii) recording a series of early responses;
(iii) determining a submaximal stimulation level for F-wave acquisition and analysis, wherein the submaximal stimulation level is an intensity level which is approximately fifty percent of a maximal stimulus intensity, and further wherein the maximal stimulus intensity is an intensity level at which additional increases in stimulus intensity do not lead to further increases in the amplitude of an evoked response;
(iv) applying a series of stimuli to a nerve, using the stimulation electrode, wherein the series of stimuli are applied at the submaximal stimulation level;
(v) recording a series of late responses;
(vi) regulating the submaximal stimulation level and acquisition condition based on late response features;
(vii) analyzing late responses to regulate the processing condition of F-wave features;
(viii) characterizing F-wave features with trace-by-trace and/or total waveform set analysis; and
(ix) comparing F-wave characteristics based on the submaximal late responses with those of normal character and those of known disorder.

38. A system for analyzing F-waves acquired under submaximal stimulation conditions, the system comprising:
(i) a stimulation electrode;
(ii) a stimulation circuit connected to the stimulation electrode for applying a series of stimuli to a nerve;
(iii) a detection electrode;
(iv) a detection circuit connected to the detection electrode; and
(v) an analyzer connected to the detection circuit and stimulation circuit and adapted to conduct submaximal F-wave analysis by:
(a) recording a series of early responses detected by the detection circuit and evoked by stimuli with variable intensities delivered by the stimulation circuit;
(b) determination of a submaximal stimulation level based on an early response feature space, wherein the submaximal stimulation level is an intensity level which is less than a maximal stimulus intensity and less than a near maximal stimulus intensity, wherein the submaximal stimulation level is an intensity level which is approximately fifty percent of a maximal stimulus intensity, and further wherein the maximal stimulus intensity is an intensity level at which additional increases in stimulus intensity do not lead to further increases in the amplitude of an evoked response;
(c) recording a series of late responses detected by the detection circuit and evoked by submaximal stimulation;
(d) regulating the stimulation circuit by the analyzer based on late response features;
(e) recording and analyzing a series of late responses detected by the detection circuit; and
(f) altering the F-wave analysis setup and late response traces; and
(vi) apparatus for characterizing the F-wave features.

39. A method for acquiring submaximal F-wave features, comprising:
(i) determining a submaximal stimulation level for submaximal F-wave acquisition, wherein the submaximal stimulation level is an intensity level which is less than a maximal stimulus intensity and less than a near maximal stimulus intensity, wherein the submaximal stimulation level is an intensity level which is approximately fifty percent of a maximal stimulus intensity, and further wherein the maximal stimulus intensity is an intensity level at which additional increases in stimulus intensity do not lead to further increases in the amplitude of an evoked response;
(ii) acquiring and analyzing late waves, using a stimulation electrode and a detection electrode, under submaximal stimulation conditions;
(iii) modifying the stimulation conditions based on real-time monitoring of the late wave analysis outcomes; and
(iv) extracting and comparing F-wave features under alternative stimulation conditions.

40. Apparatus for acquiring submaximal F-wave features, comprising:
(i) a unit for determining a submaximal stimulation level for submaximal F-wave acquisition, wherein the submaximal stimulation level is an intensity level which is less than a maximal stimulus intensity and less than a near maximal stimulus intensity, wherein the submaximal stimulation level is an intensity level which is approximately fifty percent of a maximal stimulus intensity, and further wherein the maximal stimulus intensity is an intensity level at which additional increases in stimulus intensity do not lead to further increases in the amplitude of an evoked response;
(ii) a unit for acquiring and analyzing late waves under submaximal stimulation conditions;
(iii) a unit for modifying the stimulation conditions based on real-time monitoring of the late wave analysis outcomes; and
(iv) a unit for extracting and comparing F-wave features under alternative stimulation conditions.

* * * * *